United States Patent
Schmidt et al.

(10) Patent No.: US 6,168,838 B1
(45) Date of Patent: Jan. 2, 2001

(54) FLUORINATED PHENANTRENE DERIVATIVES FOR LIQUID CRYSTAL MIXTURES

(75) Inventors: Wolfgang Schmidt, Köln; Javier Manero, Liederbach, both of (DE)

(73) Assignee: Aventis Research & Technologies GmbH & Co. KG, Frankfurt (DE)

( * ) Notice: Under 35 U.S.C. 154(b), the term of this patent shall be extended for 0 days.

(21) Appl. No.: 09/331,268

(22) PCT Filed: Dec. 16, 1997

(86) PCT No.: PCT/EP97/07059

§ 371 Date: Aug. 19, 1999

§ 102(e) Date: Aug. 19, 1999

(87) PCT Pub. No.: WO98/27035

PCT Pub. Date: Jun. 25, 1998

(30) Foreign Application Priority Data

Dec. 19, 1996 (DE) .............................. 196 53 008

(51) Int. Cl.[7] .................... C09K 19/32; C09K 19/34; C07C 23/44; C07C 43/225; C07D 471/00

(52) U.S. Cl. ............... 428/1.1; 252/299.61; 252/299.62; 544/249; 544/250; 544/251; 544/344; 544/345; 546/81; 546/82; 546/88; 568/634; 570/183; 570/187

(58) Field of Search .......................... 252/299.62, 299.61; 428/1.1; 544/249, 250, 251, 344, 345; 546/81, 82, 88; 560/5; 568/634; 570/183, 187

(56) References Cited

U.S. PATENT DOCUMENTS 5,648,021 * 7/1997 Wingen et al. ................. 252/299.62

FOREIGN PATENT DOCUMENTS

19500768 * 9/1995 (DE) .
19524230 * 1/1997 (DE) .

* cited by examiner

*Primary Examiner*—Shean C. Wu
(74) *Attorney, Agent, or Firm*—Frommer Lawrence & Haug

(57) ABSTRACT

Fluorinated phenanthrene derivatives and their use in liquid-crystalline mixtures
Fluorinated phenanthrene derivatives of the formula (I)

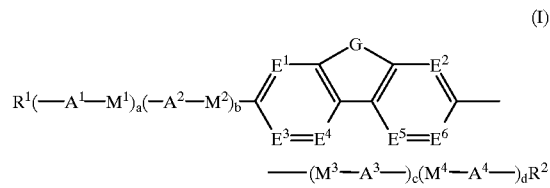

in which

G is —CHF—$CH_2$— or —CF=CH—, $E^1$, $E^2$, $E^3$, $E^4$, $E^5$ and $E^6$ are identical or different and are —CH—, —CF— or —N— and $R^1$(—$A^1$—$M^1$)$_a$(—$A^2$—$M^2$)$_b$, ($M^3$—$A^3$—)$_c$($M^4$—$A^4$—)$_d$ $R^2$ denote mesogenic radicals are suitable as components for liquid-crystalline mixtures, especially ferroelectric mixtures.

9 Claims, No Drawings

FLUORINATED PHENANTRENE DERIVATIVES FOR LIQUID CRYSTAL MIXTURES

This application is a 371 of PCT/EP97/07059, Dec 16, 1997.

DESCRIPTION

Fluorinated phenanthrene derivatives and their use in liquid-crystalline mixtures In addition to nematic and cholesteric liquid crystals, recent times have also seen the use of optically active tilted smectic (ferroelectric) liquid crystals in commercial display devices.

Clark and Lagerwall showed that the use of ferroelectric liquid crystals (FLCs) in very thin cells leads to optoelectric switching or display elements having response times faster by a factor of up to 1000 than those of the conventional TN (twisted nematic) cells (see, for example, EP-A 0 032 362). On the basis of these and other favorable properties, for example the possibility of bistable switching and the contrast, which is virtually independent of viewing angle, FLCs are in principle highly suited to applications such as computer displays.

For the use of FLCs in electrooptical or completely optical assemblies there is a need either for compounds which form tilted or orthogonal smectic phases and which are themselves optically active, or else for compounds which, although forming such smectic phases are not themselves optically active, can be doped with optically active compounds to induce ferroelectric smectic phases. The desired phase should at the same time be stable over as wide as possible a temperature range.

Obtaining a good contrast ratio in electrooptical assemblies necessitates a uniform planar orientation of the liquid crystals. Good orientation in the $S_A$ and $S^*_C$ phase can be achieved, for example, when the phase sequence of the liquid-crystal mixture with decreasing temperature is as follows:

isotropic→N*→$S_A$→$S^*_C$

A precondition is that the pitch of the helix in the N* phase is very large (greater than 10 μm) or, even better, is fully compensated (see, for example: T. Matsumoto et al., Proc. of the 6th Int. Display Research Conf., Japan Display, Sep. 30–Oct. 2, 1986, Tokyo, Japan, pp. 468–470; M. Murakami et al., ibid., pp. 344–347). This is done, for example, by adding one or more optically active dopes which induce, say, a right-handed helix to the chiral liquid-crystal mixture which in the N* phase has a left-handed helix, in amounts such that the helix is compensated.

For the use of the SSFLCD effect (Surface Stabilized Ferroelectric Liquid Crystal Display) of Clark and Lagerwall for uniform planar orientation a further precondition is that the pitch in the smectic C* phase is substantially greater than the thickness of the display element (*Mol. Cryst. Liq. Cryst.* 1983, 94, 213 and ibid. 1984, 114, 151.

The optical response time τ[μs] of ferroelectric liquid-crystal systems, which should be as short as possible, depends on the rotational viscosity of the system γ[mPas], on the spontaneous polarization $P_s$ [nC/cm$^2$] and on the electric field strength E [V/m] in accordance with the relationship

$$\tau \sim \frac{\gamma}{P_s \cdot E}$$

Since the field strength E is determined by the electrode separation in the electrooptical component and by the applied voltage, the ferroelectric display medium must be of low viscosity and must have a high spontaneous polarization in order for a short response time to be obtained.

Finally, requirements in addition to thermal, chemical and photochemical stability are for a small optical anisotropy Δn and a small positive or, preferably, negative dielectric anisotropy Δε (see, for example: S. T. Lagerwall et al., "Ferroelectric Liquid Crystals for Displays", SID Symposium, Oct. Meeting 1985, San Diego, Calif., USA).

The entirety of these requirements can only be met with mixtures of two or more components. The basis of these mixtures (or matrix) is preferably formed by compounds which as far as possible themselves already have the desired phase sequence I→N→$S_A$→$S_C$. Further components are often added to the mixture in order to lower the melting point and to broaden the $S_C$ phase and usually the N phase as well, for inducing the optical activity, for pitch compensation and for adapting the optical and dielectric anisotropy, as far as possible without increasing the rotational viscosity, for example.

Ferroelectric liquid-crystal displays can also be operated by utilizing the DHF (Distorted Helix Formation) effect or the PSFLCD (Pitch Stabilized Ferroelectric Liquid Crystal Display, also called SBF=Short Pitch Bistable Ferroelectric) effect. The DHF effect was described by B. I. Ostrovski in *Advances in Liquid Crystal Research and Applications*, Oxford/Budapest, 1980, 469 ff. and the PSFLCD effect is described in DE-A 39 20 625 and EP-A 0 405 346. In contrast to the SSFLCD effect, utilizing these effects requires a liquid-crystalline material with a short $S_C$ pitch.

Derivatives of phenanthrene (which here also includes 9,10-dihydrophenanthrenes) have already been described as liquid crystals or as components of liquid-crystalline mixtures:

Azomethines having a phenanthrene or 9,10-dihydrophenanthrene unit are known from *J. Chem. Soc.* 1958, 552 and *J. Chem. Soc., Perkin Trans. II* 1982, 465–472; keto derivatives of 9,10-dihydrophenanthrene are known from *Chem. Ind.* [London] 1974, 615, *Prod Int. Liq. Cryst. Conf.* 1973, 397 and *Tetrahedron* 1981, 37, 2815; carboxyl derivatives of 9,10-dihydrophenanthrene are known from DD-WP 153 826 and *Z. Chem.* 1983, 23, 21–22; 2,7-bis(alkoxy)phenanthrenes are known from *Nippon Kagaku Kaishi* 1980, 250; and phenanthrene derivatives having one or more fluorine substituents in positions 1, 3, 4, 5, 6 and 8 are known from DE-A 19 500 768. However, since the development—of ferroelectric liquid-crystal mixtures in particular—can in no way be regarded as complete, the manufacturers of displays are interested in a very wide variety of components for mixtures. One of the reasons for this is that only the interaction of the liquid-crystalline mixtures with the individual components of the display device or of the cells (for example the alignment layer) allows conclusions to be drawn about the quality of the liquid-crystalline mixtures too.

The object of the present invention was therefore to provide compounds which are suitable in liquid-crystalline mixtures for improving the profile of properties of these mixtures.

It has now been found, surprisingly, that phenanthrene derivatives of the formula (I) are particularly suitable for use in liquid-crystal mixtures.

The invention therefore provides compounds of the formula (I)

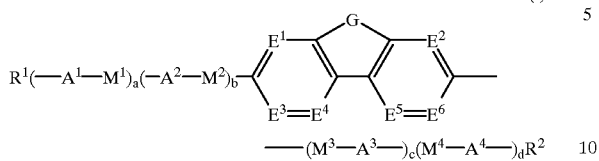

(I)

in which the symbols and indices have the following meanings:

G is —CHF—CH$_2$— or —CF=CH—;

$E^1$, $E^2$, $E^3$, $E^4$, $E^5$ and $E^6$ are identical or different and are
—CH—, —CF— or —N—, with the proviso that $E^4$ and $E^5$ cannot simultaneously be —N—;

$R^1$ and $R^2$ are identical or different and are a) hydrogen, —F, —Cl, —CF$_3$, —OCF$_3$ or —CN, b) a straight-chain or branched alkyl radical (with or without an asymmetric carbon atom) having 1 to 20 carbon atoms, where b1) one or more nonadjacent and nonterminal CH$_2$ groups can be replaced by —O—, —S—, —CO—O—, —O—CO—, —O—CO—O— or —Si(CH$_3$)$_2$—, and/or b2) one or more CH$_2$ groups can be replaced by —CH=CH—, —C≡C—, cyclopropane-1,2-diyl, 1,4-phenylene, 1,4-cyclohexylene or 1,3-cyclopentylene, and/or b3) one or more H atoms can be replaced by F and/or Cl, and/or b4) the terminal CH$_3$ group can be replaced by one of the following chiral groups (optically active or racemic):

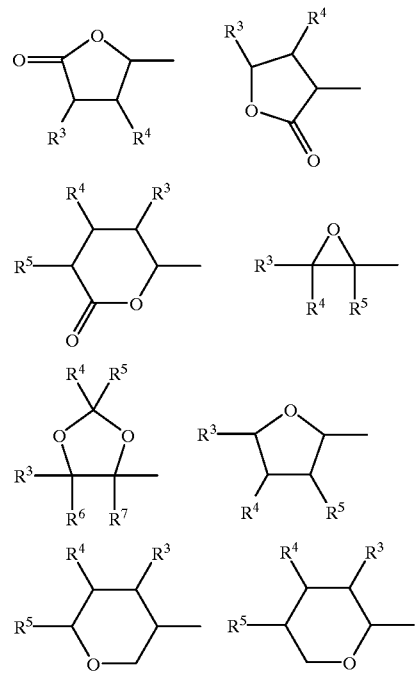

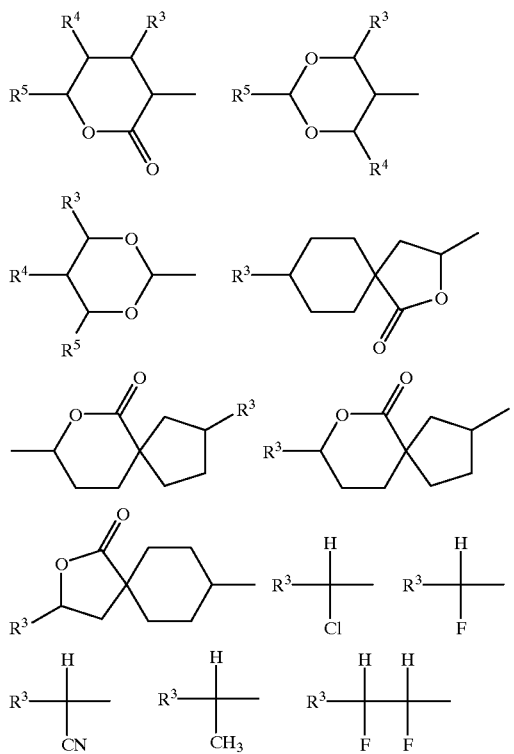

with the proviso that only one of the radicals $R^1$, $R^2$ can be hydrogen, —F, —Cl, —CF$_3$, —OCF$_3$ or —CN;

$R^3$, $R^4$, $R^5$, $R^6$ and $R^7$ are identical or different and are a) hydrogen, b) a straight-chain or branched alkyl radical (with or without an asymmetric carbon atom) having 1 to 16 carbon atoms, where b1) one or more nonadjacent and nonterminal CH$_2$ groups can be replaced by —O—, and/or b2) one or two CH$_2$ groups can be replaced —CH=CH—, c) $R^4$ and $R^5$ together are alternatively —(CH$_2$)$_4$— or —(CH$_2$)$_5$—, if they are attached to an oxirane, dioxolane, tetrahydrofuran, tetrahydropyran, butyrolactone or valerolactone system;

$M^1$, $M^2$, $M^3$ and $M^4$ are identical or different and are
—CO—O—, —O—CO—, —CO—S—, —S—CO—, —CS—O—, —O—CS—, —CH$_2$—O—, —O—CH$_2$—, —CH$_2$—S—, —S—CH$_2$—, —CH=CH—, —C≡C—, —CH$_2$—CH$_2$—CO—O—, —O—CO—CH$_2$—CH$_2$— or a single bond;

$A^1$, $A^2$, $A^3$ and $A^4$ are identical or different and are
1,4-phenylene in which one or more H atoms can be replaced by F, Cl and/or CN, pyrazine-2,5-diyl, in which one or two H atoms can be replaced by F, Cl and/or CN, pyridazine-3,6-diyl in which one or two H atoms can be replaced by F, Cl and/or CN, pyridine-2,5-diyl in which one or more H atoms can be replaced by F, Cl and/or CN, pyrimidine-2,5-diyl in which one or two H atoms can be replaced by F, Cl and/or CN, 1,4-cyclohexylene in which one or two H atoms can be replaced by CN, F and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom can be replaced by F, Cl and/or CN, 1,3-thiazole-2,5-diyl in which one H atom can be replaced by F, Cl and/or CN, thiophene-2,4-diyl, in which one H atom can be replaced by F, Cl and/or CN, thiophene-2,5-diyl in which one or two H atoms can be replaced by F, Cl and/or CN, piperazine-1,4-diyl or piperazine-2,5-diyl or 1-($C_1$–$C_4$)alkyl-1-silacyclohexylene-1,4-diyl;

a, b, c and d are zero or one, with the proviso that the compound of the formula (I) may contain no more than four ring systems having five or more members.

The provision of compounds of the formula (I) considerably broadens, in general terms, the palette of liquid-crystalline substances which from a variety of applications-related standpoints are suitable for the preparation of liquid-crystalline mixtures.

In this connection the compounds of the formula (I) possess a broad scope of application. Depending on the selection of the substituents they can be used as base materials forming the predominant part of liquid-crystalline phase compositions; or alternatively, compounds of the formula (I) can also be added to liquid-crystalline base materials from other classes of compounds, in order for example to influence the dielectric and/or optical anisotropy of such a dielectric material and/or to optimize its threshold voltage and/or its viscosisty.

The compounds of the formula (I) are particularly suitable for addition even in small amounts for influencing the dielectric anisotropy (As) toward higher negative values.

The novel compounds of the formula (I) are particularly suitable for use in FLC mixtures for ferroelectric switching and/or display devices which are operated in inverse mode. Preference is given to compounds of the formula (I) in which $E^1$ and $E^2$ are identical or different and are —CH—, —CF— or —N— and $E^3$, $E^4$, $E^5$ and $E^6$ are identical or different and are —CH— or —CF—.

Particular preference is given to compounds of the formula (I) in which $E^3$, $E^4$, $E^5$ and $E^6$ are identical and are —CH—.

Very particular preference is given to compounds of the formula (I) in which $E^1$, $E^2$, $E^3$, $E^4$, $E^5$ and $E^6$ are identical and are —CH— or in which $E^3$, $E^4$, $E^5$, $E^6$ are identical and are —CH— and $E^1$ and $E^2$ are identical and are —CF—.

Special preference is given to the compounds of the formula (I) in which $E^1$, $E^2$, $E^3$, $E^4$, $E^5$ and $E^6$ are identical and are —CH—.

Preferably, $R^1$ and $R^2$ are identical or different and are a) hydrogen, —CN or F.

b) a straight-chain or branched alkyl radical (with or without an asymmetric carbon atom) having 1 to 18 carbon atoms, where
  b1) one or more nonadjacent and nonterminal $CH_2$ groups can be replaced by —O—, —CO—O—, —O—CO—, —O—CO—O or —Si(CH$_3$)$_2$—, and/or
  b2) one $CH_2$ group can be replaced by cyclopropane-1,2-diyl, 1,4-phenylene or trans-1,4-cyclohexylene, and/or
  b3) one or more H atoms can be replaced by F, and/or
  b4) the terminal $CH_3$ group can be replaced by one of the following chiral groups (optically active or racemic):

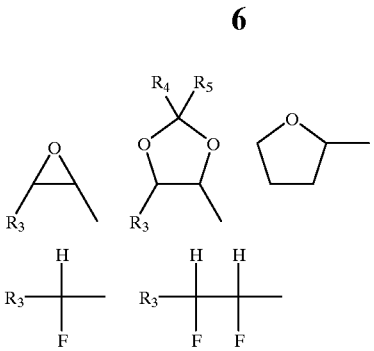

with the proviso that only one of the radicals $R^1$ and $R^2$ can be —H, —F or —CN.

With particular preference $R^1$ and $R^2$ are identical or different and are a) hydrogen, b) a straight-chain or branched alkyl radical (with or without an asymmetric carbon atom) having 1 to 16 carbon atoms, where
  b1) one or two nonadjacent and nonterminal $CH_2$ groups can be replaced by —O—, —CO—O—, —O—CO—, —O—CO—O— or —Si(CH$_3$)$_2$—, and/or
  b2) one $CH_2$ group can be replaced by 1,4-phenylene or trans-1,4-cyclohexylene, and/or
  b3) one or more H atoms can be replaced by F, and/or
  b4) the terminal $CH_3$ group can be replaced by one of the following chiral groups (optically active or racemic):

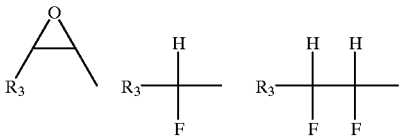

with the proviso that only one of the radicals $R^1$ and $R^2$ can be H.

$R^3$, $R^4$, $R^5$, $R^6$ and $R^7$ are, preferably, identical or different and are a) hydrogen, b) a straight-chain or branched alkyl radical (with or without an asymmetric carbon atom) having 1 to 14 carbon atoms, where
  b1) one or two nonadjacent and nonterminal $CH_2$ groups can be replaced by —O—, and/or
  b2) one $CH_2$ group can be replaced by —CH=CH—, c) $R^4$ and $R^5$ together are alternatively —(CH$_2$)$_4$— or —(CH$_2$)$_5$—, if they are attached to an oxirane, dioxolane, tetrahydrofuran, tetrahydropyran, butyrolactone or valerolactone system.

$R^3$, $R^4$, $R^5$, $R^6$ and $R^7$ are, with particular preference, identical or different and are a) hydrogen, b) a straight-chain or branched alkyl radical (with or without an asymmetric carbon atom) having 1 to 14 carbon atoms, where
  b1) one nonterminal $CH_2$ group can be replaced by —O—, and/or c) $R^4$ and $R^5$ together are alternatively —(CH$_2$)$_4$— or —(CH$_2$)$_5$—, if they are attached to an oxirane, dioxolane, tetrahydrofuran, tetrahydropyran, butyrolactone or valerolactone system.

Preferably, $M^1$, $M^2$, $M^3$ and $M^4$ are identical or different and are

—CO—O—, —O—CO—, —CH$_2$—O—, —O—CH$_2$—, —CH=CH—, —C≡C—, —CH$_2$—CH$_2$—CO—O, —O— CO—CH$_2$—CH$_2$— or a single bond.

With particular preference, $M^1$, $M^2$, $M^3$ and $M^4$ are identical or different and are —CO—O—, —O—CO—, —CH$_2$—O—, —O—CH$_2$— or a single bond.

Preferably, $A^1$, $A^2$, $A^3$ and $A^4$ are identical or different and are 1,4-phenylene in which one or two H atoms can be replaced by F and/or CN, pyridine-2,5-diyl, in which one or two H atoms can be replaced by F and/or CN, pyrimidine-2,5-diyl in which one or two H atoms can be replaced by F and/or CN, trans-1,4-cyclohexylene in which one or two H atoms can be replaced by CN and/or F, 1,3,4-thiadiazole-2,5-diyl, 1,3-dioxane-2,5-diyl, 1,3-thiazole-2,4-diyl, in which one H atom can be replaced by F, 1,3-thiazole-2,5-diyl in which one H atom can be replaced by F, or thiophene-2,5-diyl in which one or two H atoms can be replaced by F.

With particular preference, $A^1$, $A^2$, $A^3$ and $A^4$ are identical or different and are 1,4-phenylene in which one or two H atoms can be replaced by F, pyridine-2,5-diyl in which one H atom can be replaced by F, pyrimidine-2,5-diyl, trans-1,4-cyclohexylene in which one or two H atoms can be replaced by CN and/or F, 1,3,4-thiadiazole-2,5-diyl, 1,3-thiazole-2,5-diyl or thiophene-2,5-diyl.

Very particular preference is given to the following compounds of the formula (Ia) to (If):

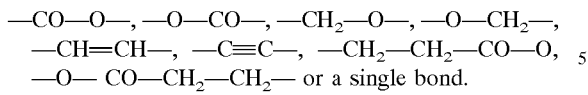

(Ia)

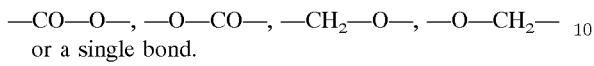

(Ib)

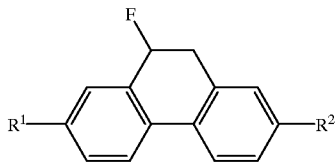

(Ic)

(Id)

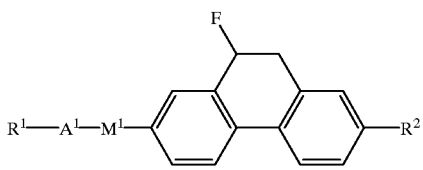

(Ie)

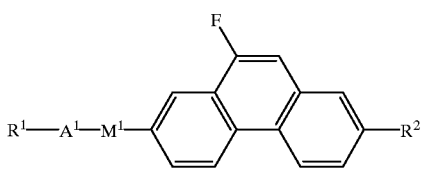

(If)

in which $R^1$, $R^2$, $M^1$, $M^3$, $A^1$ and $A^3$ have the meanings and preferences stated above.

The compounds according to the invention are prepared by methods known per se from the literature, as are described in standard works on organic synthesis, for example Houben-Weyl, Methoden der Organischen Chemie, Georg-Thieme-Verlag, Stuttgart.

The preparation is carried out under reaction conditions which are known and suitable for said reactions. Use may also be made here of variants which are known per se but which are not mentioned here in any more detail.

If desired, the starting materials can also be formed in situ, by not isolating them from the reaction mixture but instead immediately converting them further into the compounds of the formula (I).

By way of example, synthesis routes to 9-fluorophenanthrene, 9-fluoro-9,10-dihydrophenanthrene and compounds of the formula (I) are indicated in schemes 1 to 6, although other methods are also conceivable and possible.

Scheme 1

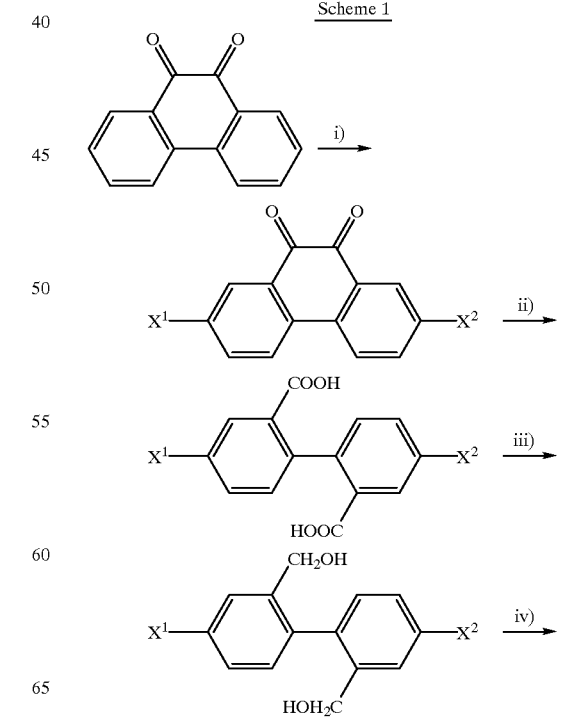

9
-continued

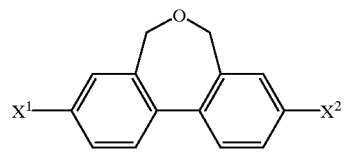

Synthesis of 5,7-dihydrodibenz[c,e]oxepines as precursors for compounds of the formula (I) starting from commercial phenanthrene quinone. $X^1$, $X^2$ = H, Br, I, $NO_2$, $NH_2$. i) see Beilsteins Handbuch der organischen Chemie, Vol. 7, cited literature, ii) 1. CuCl/pyridine/$O_2$, 2. HCl, Synthesis 1982, 731–732; iii) LiAlH$_4$/Et$_2$O, J. Org. Chem. 1953, 18, 801–805 or 1. MeOH/H$^+$, 2. LiBH$_4$/Et$_2$O, Chem. Ber. 1951, 84, 627–632; iv) HBr/H$_2$O, Chem. Ber. 1951, 84, 627–632 or potassium bisulfate/160 C, J. Org. Chem. 1953, 18, 801–805, Chem. Ber. 1951, 84, 627–632 or (CF$_3$SO$_2$)$_2$O/pyridine/CH$_2$Cl$_2$, Angew. Chem. 1996, 108, 1640–1642.

The preparation of 2-mono- and 2,7-disubstituted phenanthrene quinones (Scheme 1,5) where $X^1$, $X^2$=H, Br, I, $NO_2$, $NH_2$ has been described on several occasions, for example in Beilsteins Handbuch der organischen Chemie, Springer-Verlag, Berlin, Vol. 7 (main and supplementary series) and in the literature cited therein.

Scheme 2

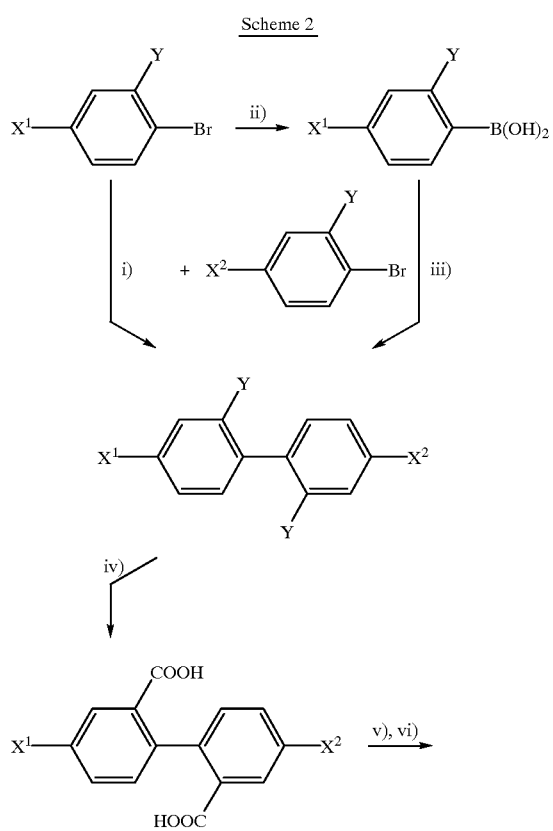

10
-continued

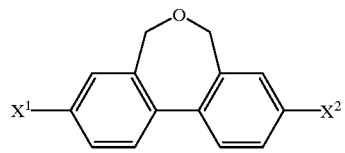

Synthesis of 5,7-dihydrodibenz[c,e]oxepines as precursors for compounds of the formula (I) by way of aromatic coupling reactions. Y = 5-alkyl-4,5-dihydrooxazol-2-yl or ——CONR$_2$; R = e.g. Et, i-Pr; $X^1$ = H, NO$_2$, OR'; $X^2$ = H, NO$_2$, Cl, OR'; R' = e.g. alkyl or tertbutyldimethylsilyl, benzyl, dihydropyranyl or another suitable protecting group. i) Cu/DMF, Angew. Chem. 1996, 108, 1640–1642; ii) 1. Mg/THF or n-BuLi/THF 2. B(OMe)$_3$, 3. H$^+$, Liq. Cryst. 1996, 21, 279–289, WO 96/00710 or Tetrahedron Lett.1985, 26, 5997-6000; iii) Pd$^0$ cat., Tetrahedron Lett. 1988, 29, 5459–5462, cited literature; iv) 1. TFA, H$_2$O, 2. Ac$_2$O/pyridine, 3. tBuOK/THF/H$_2$O, Angew. Chem. 1996, 108, 1640-1642; v), vi) cf. Scheme 1.

Scheme 3

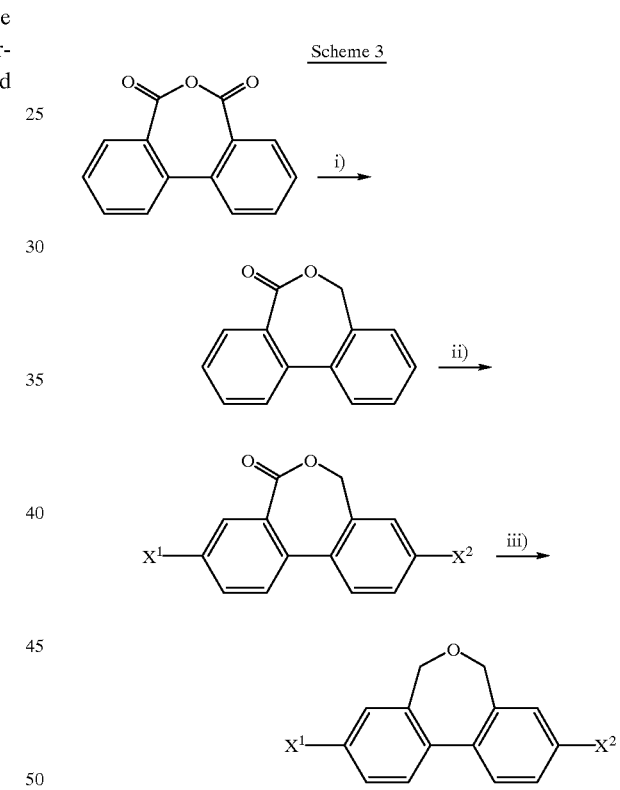

Synthesis of 5,7-dihydrodibenz[c,e]oxepines as precursors for compounds of the formula (I) starting from diphenic anhydride. $X^1$, $X^2$ = H, NO$_2$, NH$_2$; i) NaBH$_4$/DMF, Tetrahedron 1989, 45, 1365–1376, V. Brandmeier, Dissertation, University of Erlangen-Nuremberg, 1989; ii) HNO$_3$/H$_2$SO$_4$, V. Brandmeier, Dissertation, University of Earlangen-Nuremberg, 1989; iii) Zn/HCl conc./EtOH, V. Brandmeier. Dissertation, University of Erlangen-Nuremberg, 1989.

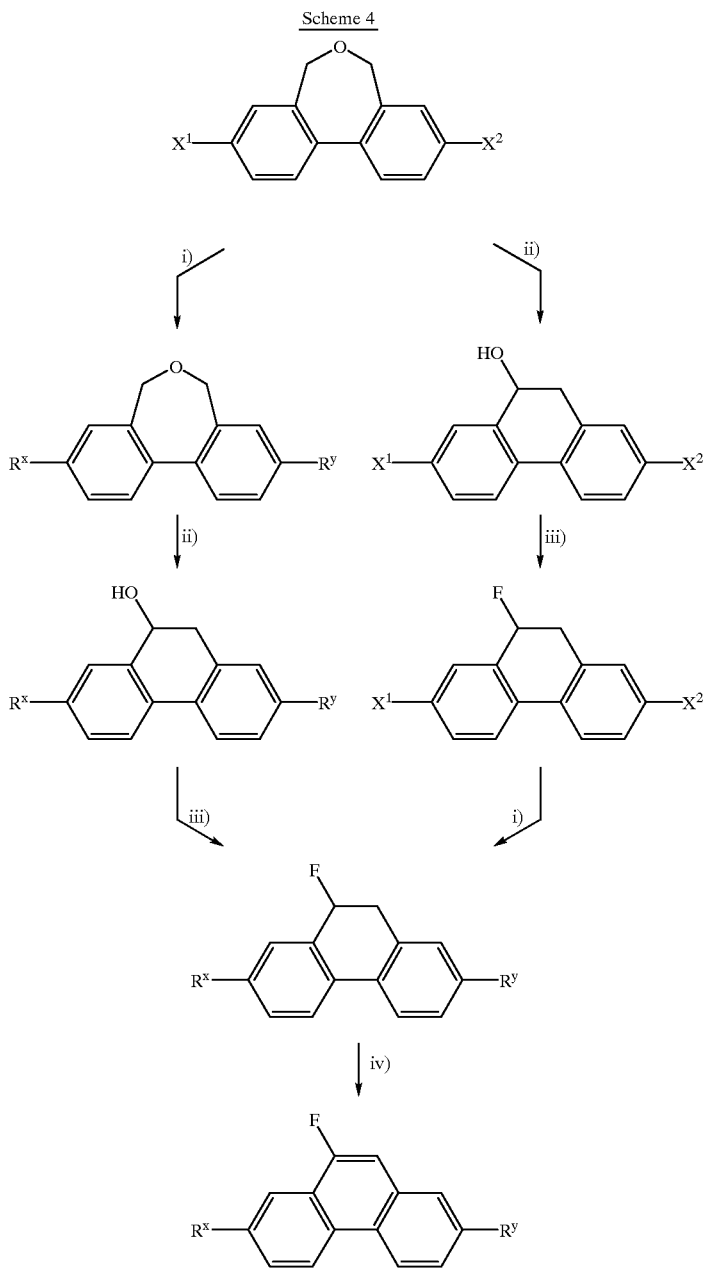

Synthesis of compounds of the formula (I) starting from 5,7-dihydrodibenz[c,e]oxepines. $X^1$, $X^2$: see Schemes 1 to 3. i) for the synthesis and coupling of the groups $R^x$ and $R^y$ see the following section; ii) $KNH_2/NH_3$, J. Org Chem. 1953, 18, 801–805 or $PhLi/Et_2O$, Chem Ber. 1951, 84, 627–632; iii) $DAST/CH_2Cl_2$, J. Org. Chem. 1975,40, 574–578; iv) DDQ, J. Chem. Soc. 1954, 3569–3574.

The positional isomers which may possibly be formed in the course of the rearrangement of 5,7-dihydrodibenz[c,e] oxepines into 9,10-dihydro-9-phenanthroles (reaction step ii in Scheme 4) and in the dehydrohalogenation of 9,10-difluoro-9,10-dihydrophenanthrenes (reaction step vi in Scheme 5) with asymmetric substitution ($X^1 \neq X^2$ and/or $R^x \neq R^y$) can be resolved subsequently or in one of the subsequent stages by means, for example, of column chromatography.

An alternative synthesis route (Scheme 5) starts from commercial phenanthrene quinone and leads via 9,10-dihydrophenanthrene-9,10-diol and 9,10-difluoro-9,10-dihydrophenanthrene to compounds of the formula (I).

Scheme 5

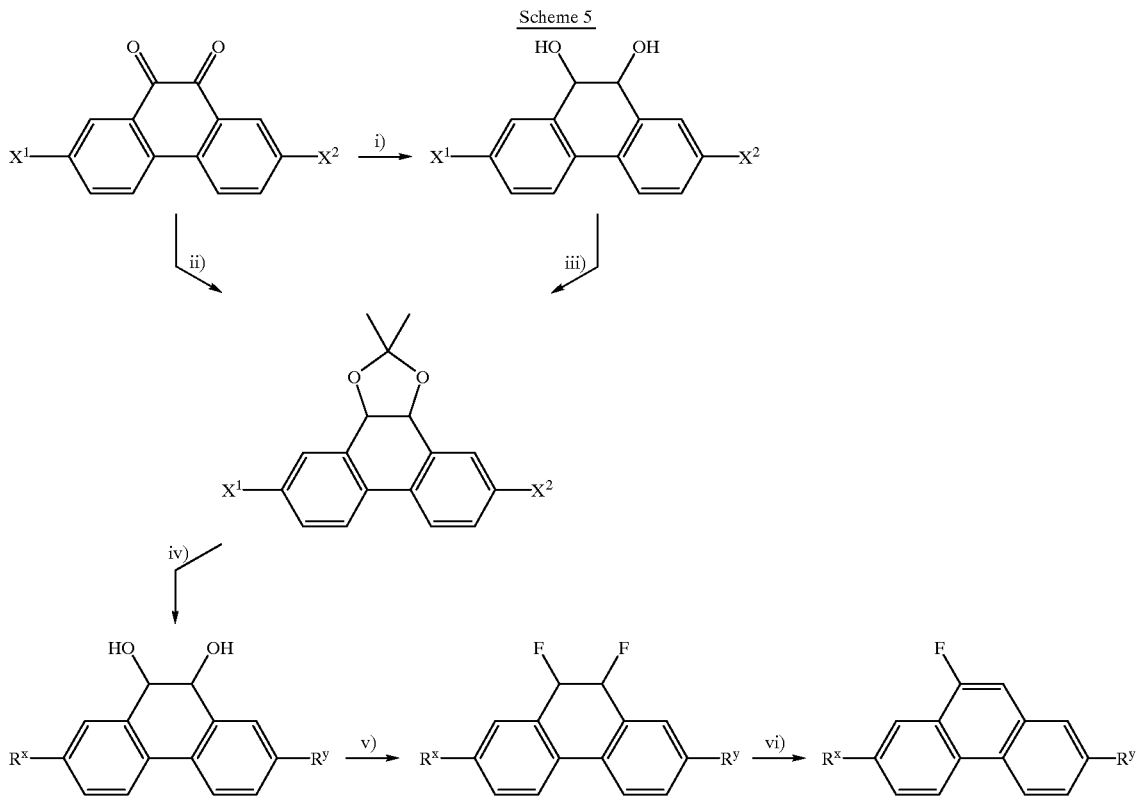

Synthesis of compounds of the formula (I) via 9,10-dihydrophenanthrene-9,10-diol. $X^1$, $X^2$: see Scheme 1. i) LiAlH$_4$/Et$_2$O or NaBH$_4$/Et$_2$O, J. Org. Chem.1957, 22, 1651–1658, J. Org. Chem. 1959, 24, 86–90, J. Chem. Soc. 1950, 1188–1190; ii) 2-nitropropane/Me$_4$NOH/CH$_3$CN, J. Chem.Soc., Perkin Trans II 1996, 1429–1433; iii) Acetone, toluene, 4-TosOH, Organikum, 15th ed., VEB Deutscher Verlag der Wissenschaften, Berlin, 1984, Chap. D.7.1.2., Liq. Cryst. 1989, 5, 197–207; iv) H$^+$/H$_2$O, Organikum, 15th ed., VEB Deutscher Verlag der Wissenschaften, Berlin, 1984, Chap. D.7.1.2.; for the synthesis and coupling of the groups $R^x$ and $R^y$ see thje following section; v) DAST/CH$_2$Cl$_2$, J. Org. Chem. 1975, 40, 574–578; vi) KOH/MeOH or DBU, Organikum, 15th ed., VEB Deutscher Verlag der Wissenschaften, Berlin, 1984, Chap. D.3.1.5., Methoden der organischen Chemie (Houben-Weyl), Vol. V/1b, Georg Thieme Verlag, Stuttgard, 1972.

Scheme 6 indicates by way of example the synthesis of asymmetrically substituted compounds of the formula (I) via the corresponding biphenyl-2-carbaldehyde and 9,9-difluoro-9,10-dihydrophenanthrene.

Scheme 6

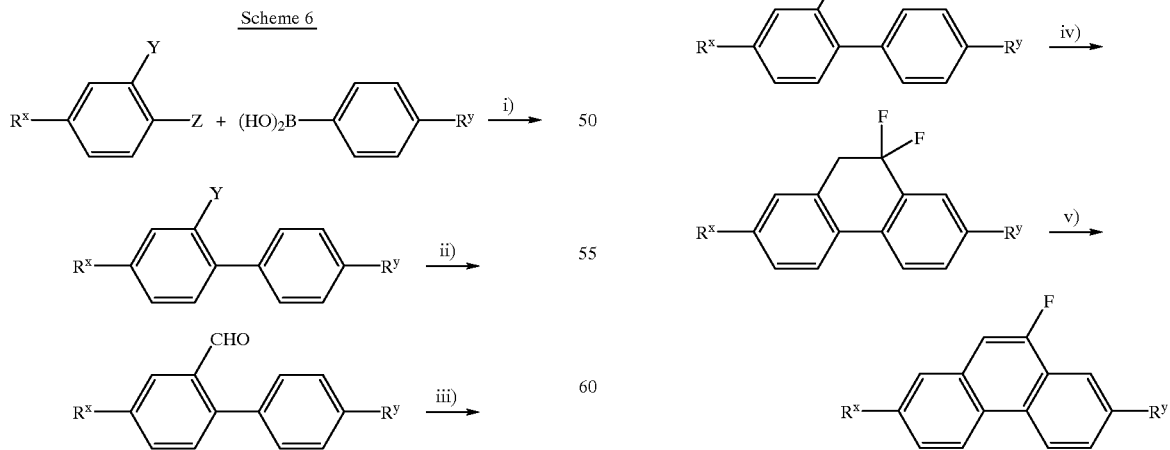

-continued

Synthesis of compounds of the formula (I) via biphenyl-2-carbaldehydes. Z = I, Br, Cl; Y = ———CH(OMe)$_2$, ———CN, ———CONEt$_2$.

i) Pd$^0$-cat., EP 694 530; ii) for Y ══CH(OMe)$_2$: H$^+$/H$_2$O, Organikum, 15th ed., VEB Deutscher Verlag der Wissenschaften, Berlin, 1984, Chap. D.7.1.2., for Y = ———CN, ———CONEt$_2$: Li(EtO)$_3$AlH/THF or SnCl$_2$/Et$_2$O/HCl or 1. Ti(OiPr)$_4$Ph$_2$SiH$_2$, 2. H$_3$O$^+$, Angew. Chem. 1996, 108, 1662–1664, cited literature; iii) PPh$_3$/ClF$_2$CCO$_2$Na, diglyme, Angew. Chem. 1982, 94, 795 or CF$_2$Br$_2$/PPh$_3$/Zn/N,N-dimethylacetamide, Chem Lett. 1979, 983–986; iv) hv, Angew. Chem. 1982, 94, 795; v) KOMe/MeOH, Angew. Chem. 1982, 94, 795.

The group $R^x$ is equivalent to the group $R^1$—$(A^1$—$M^1)_a$—$(A^2$—$M^2)_b$ or an appropriate unprotected or protected precursor thereof which in later steps can be converted into this group by methods which are known per se and are familiar to the skilled worker.

The group $R^y$ is equivalent to the group $(M^3$—$A^3)_c$—$(M^4$—$A^4)_d$—$R^2$ or an appropriate unprotected or protected precursor thereof which in later steps can be converted into this group by methods which are known per se and are familiar to the skilled worker.

The radical $R^x$ or $R^y$ is synthesized by methods which are known per se and are familiar to the skilled worker. Its preparation takes place under reaction conditions which are known and suitable for said reactions. In this context it is also possible to make use of variants which are known per se and are not mentioned in any more detail here.

Reference may be made, for example, to DE-A 23 44 732, 24 50 088, 24 29 093, 25 02 94, 26 36 684, 27 01 591 and 27 52 975 for compounds with 1,4-cyclohexylene or 1,4-phenylene groups; to DE-A 26 41 724 for compounds with pyrimidine-2,5-diyl groups; to DE-A 40 26 223, EP-A 0 391 203 and German Patent Application 196 48 171.6 for compounds with pyridine-2,5-diyl groups; to DE-A 32 31 462 for compounds with pyridazine-3,6-diyl groups; and to EP-A 309 514 for compounds with 1,3,4-thiadiazole-2,5-diyl groups and to EP-A 0 630 903 for compounds with 1-sila-1,4-cyclohexylen groups.

Reference may additionally be made to *Tetrahedron Lett.* 1981, 37, 2815–1821, *ibid.* 1985, 26, 61–64 and *Z. Chem.* 1983, 23, 21–22 for the introduction of alkyl and acyl substituents, to *Bioorg. Med. Chem. Lett.* 1996, 6, 481–484 for the introduction of bromine, chlorine and carboxyl substituents into positions 2 and 7 of a 9,10-dihydrophenanthrene structure.

The preparation of disubstituted pyridines, disubstituted pyrazines, disubstituted pyrimidines and disubstituted pyradazines is also given, for example, in the corresponding volumes of the series "The Chemistry of Heterocyclic Compounds" by A. Weissberger and E. C. Taylor (editors).

Dioxane derivatives are judiciously prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example strong acid such as sulfuric acid, benzene- or 4-toluenesulfonic acid, at temperatures between about 20° and about 150° C., preferably between 80° C. and 120° C. Primarily suitable as reactive derivatives of the starting materials are acetals.

Some of said aldehydes and 1,3-diols and their reactive derivatives are known while some can be prepared without difficulty by standard methods of organic chemistry from compounds known from the literature. For example, the aldehydes are obtainable by oxidation of corresponding alcohols or by reduction of nitrites or corresponding carboxylic acids or derivatives thereof, and the diols by reduction of corresponding diesters.

2,3-Difluorophenylboronic acid and 4-alkoxy-2,3-difluorophenylboronic acids are described, for example, in WO 96/00710; 4-benzyloxy-2,3-difluorophenylboronic acid as well can be obtained analogously (WO 96/01246). Examples of 4-alkyl-substituted 2,3-difluorophenylboronic acids are given in EP-A 0 363 458.

Compounds in which an aromatic ring is substituted by at least one F atom can also be obtained from the corresponding diazonium salts by replacement of the diazonium group with a fluorine atom, for example by the methods of Balz and Schiemann.

As far as the linking of ring systems to one another is concerned, reference may be made, for example, to: N. Miyaura, T. Yanagai and A. Suzuki in *Synthetic Communications* 1981, 11, 513–519; DE-C39 30 663; M. J. Sharp, W. Cheng, V. Snieckus in *Tetrahedron Lett.* 1987, 28, 5093; G. W. Gray in *J. Chem. Soc. Perkin Trans. II* 1989, 2041 and *Mol. Cryst. Liq. Cryst.* 1989, 172, 165, *ibid.* 1991, 204, 43 and *ibid.* 1991, 204, 91; N. A. Bumagin; E. V. Luzikova, I. P. Letskaya, *Zh. Org. Khim.* 1995, 31, 1657–1662; EP-A 0 449 015; WO-A 89/12039; WO-A 89/03821; EP-A 0 354 434 for the direct linking of aromatics and heteroaromatics; DE-A 32 01 721 for compounds with —CH$_2$CH$_2$—bridges, and K. Seto et al. in *Liq. Cryst.* 1990, 8, 861–870 for compounds containing —C≡C— bridges.

The syntheses of 1-azaphenanthrene-5,6-dione, 4-azaphenanthrene-5,6-dione, 1,7-phenanthroline-5,6-dione and 4,7-phenanthroline-5,6-dione as starting materials for compounds of the formula (I) in accordance with Scheme 5 are described in *Synth. Commun.* 1996, 26, 2197–2203, *J. Chem. Soc., Perkin Trans. II* 1996, 7, 1429–1433 and the literature cited therein. Because of their property of being strong transition metal complexing agents, analogous derivatives of 1,10-phenanthroline are less suitable as constituents of liquid-crystalline mixtures for use in electrooptical assemblies.

Esters of the formula (I) can also be obtained by esterification of corresponding carboxylic acids (or reactive derivatives thereof) using alcohols or phenols (or reactive derivatives thereof). Another suitable example of a method for this purpose is the DCC method (DCC=dicyclohexylcarbodiimide; cf.: B. Neises, W. Steglich, *Angew. Chem.* 1978, 90, 556–557).

The corresponding carboxylic acids and alcohols and phenols are either known or can be prepared analogously to known processes.

Particularly suitable reactive derivatives of said carboxylic acids are the acid halides, especially the chlorides and bromides, and also the anhydrides, including mixed anhydrides, for example, azides or esters, especially alkyl esters having 1–4 carbon atoms in the alkyl group.

Particularly suitable reactive derivatives of said alcohols and phenols are the corresponding metal alcoholates or phenolates, preferably of an alkali metal such as sodium or potassium.

The esterification is advantageously carried out in the presence of an inert solvent. Particularly suitable solvents are ethers, such as diethyl ether, di-n-butyl ether, tetrahydrofuran, dioxane or anisole, ketones, such as acetone, butanone or cyclohexanone, amides, such as dimethylformamide or hexamethylphosphoramide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Esters of the formula (I) can also be obtained from the corresponding carboxylic acid salts (preparation by analogy with DE-C$_{4304756}$) by reaction with phenols in accordance with DE-A 4427198.

Ethers of the formula (I) are also obtainable by etherification of corresponding hydroxy compounds, preferably corresponding phenols, where the hydroxy compound is judiciously first of all converted into a corresponding metal derivative, for example into the corresponding alkali metal alcoholate or alkali metal phenolate by treatment with NaH, NaNH$_2$, NaOH, KOH, Na$_2$CO$_3$ or K$_2$CO$_3$. This product can then be reacted with the corresponding alkyl halide, alkylsulfonate or dialkyl sulfate, judiciously in an inert solvent such as acetone, 1,2-dimethoxyethane, dimethylformamide or dimethyl sulfoxide, or else with an excess of aqueous or aqueous-alcoholic NaOH or KOH at temperatures of between about 20° C. and 100° C.

Also suitable for etherification, for example, is the reaction of phenols with alcohols using diethyl azodicarboxylate and triphenylphosphine in accordance with the so-called Mitsunobu method (cf.: 0. Mitsunobu, *Synthesis* 1981, 1–28 or L. Navailles, H. T. Nguyen, P. Barois, *Liq. Cryst.* 1996, 20, 653–664).

The corresponding alcohols, alkyl halides, alkylsulfonates and dialkyl sulfates are either known or can be prepared in analogy to known methods.

Regarding the synthesis of specific radicals R$^1$ and R$^2$, reference may additionally be made, for example, to:

EP-A 0 355 008 for compounds with silicon-containing side chains,

EP-A 0 318 423 and EP-A 0 398 155 for compounds with cyclopropyl groups in the side chain, EP-A 0 292 954 for optically active compounds with an oxirane ester unit, EP-A 0 263 437 for optically active compounds with an oxirane ether unit, EP-A 0 361 272 for optically active compounds with a dioxolane ester unit, EP-A 0 351 746 for optically active compounds with a dioxolane ether unit, U.S. Pat. No. 5,051,506 for optically active compounds with a 2,3-difluoroalkyloxy unit, U.S. Pat. No. 4,798,680 for optically active compounds with a 2-fluoroalkyloxy unit, U.S. Pat. No. 4,855,429 for optically active compounds with a 2-chloroacyl unit, EP-A 552 658 for compounds with cyclohexylpropionic acid radicals chain, and EP-A 0 318 423 for compounds with cyclopropylgroups in the side chain.

The compounds according to formula (I) are especially useful for operating in smectic and nematic liquid crystal mixtures, in the case of nematic mixtures preferably for active matrix displays (AM-LCD).-(e.g. C. Prince, Seminar Lecture Notes, Volume I, p. M-3/3-M-22, SID International Symposium 1997, B. B. Bahadur, Liquid Crystal Applications and Uses, Vol.1, p.410, World Scientific—Publishing, 1990, E. Lüder, Recent Progress of AM LCD's, Proceedings of the 15$^{th}$ International Displays Research Conference, 1995, p.9–12) and in-plane-switching displays (IPS-LCD), in the case of smectic liquid crystal mixtures peferably for chirally inclined smectic (ferroelectric or antiferroelectric) displays, for ELB displays (electrically controlled birefringence) and for electroclinic displays.

The invention also provides for the use of compounds of the formula (I) in liquid-crystal mixtures, preferably smectic and nematic mixtures, especially ferroelectric mixtures. Especially preferred is the use in ferroelectric mixtures, which are operated in inverse mode.

The invention additionally provides liquid-crystal mixtures, preferably smectic and nematic mixtures, especially preferred ferroelectric and antiferroelectric, especially ferroelectric mixtures, comprising one or more compounds of the formula (I).

The smectic and nematic liquid crystal mixtures are preferable applicable for electrooptic displays, in the case of nematic mixtures especially for active matrix displays and in-plane-switching displays (IPS-LCD), in the case of smectic liquid crystal mixtures for ELB displays, for electroclinic displays and chirally inclined smectic (ferroelectric or antiferroelectric) displays.

The novel liquid-crystal mixtures generally contain from 2 to 35, preferably from 2 to 25 and, with particular preference, from 2 to 20 components.

They generally contain from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, of the novel compounds of the formula (I).

Further components of liquid-crystal mixtures comprising novel compounds of the formula (I) are preferably selected from known compounds having smectic and/or nematic and/or cholesteric phases. These include, for example:

derivatives of phenylpyrimidine as described, for example, in WO 86/06401 and U.S. Pat. No. 4,874,542, meta-substituted aromatic compounds having a six-membered ring, as described, for example, in EP-A 0 578 054, silicon compounds as described, for example, in EP-A 0 355 008, mesogenic compounds having only one side chain, as described, for example in EP-A 0 541 081, pyridylpyrimidines as described, for example, in WO 92/12974 and German Patent Application 196 48 171.6, hydroquinone derivatives as described, for example, EP-A 0 603 786, phenylbenzoates as described, for example, in P. Keller, *Feffoelectrics* 1984, 58, 3 and J. W. Goodby et al., *Liquid Crystals and Ordered Fluids*, Vol.4, New York, 1984, and thiadiazoles as described, for example, in EP-B 0 309 514.

Examples of suitable chiral, nonracemic dopes are:

optically active phenylbenzoates as described, for example, in P. Keller, *Ferroelectrics* 1984, 58, 3 and J. W. Goodby et al., *Liquid Crystals and Ordered Fluids*, Vol. 4, New York, 1984, optically active oxirane ethers as described, for example, in EP-A 0 263 437 and WO-A 93/13093, optically active oxirane esters as described, for example, in EP-A 0 292 954, optically active dioxolane ethers as described, for example, in EP-A 0 351 746, optically active dioxolane esters as described, for example, in EP-A 0 361 272, optically active tetrahydrofuran-2-carboxylic esters as described, for example, in EP-A 0 355 561, and optically active 2-fluoroalkyl ethers as described, for example, in EP-A 0 237 007 and U.S. Pat. No. 5,051, 506.

Suitable additional components of mixtures are set out in particular in the international patent application WO-A 97/04039, which is expressly incorporated herein by reference.

Preferred additional components of FLC mixtures used in the inverse mode are: phenanthrenederivatives of the formula (II),

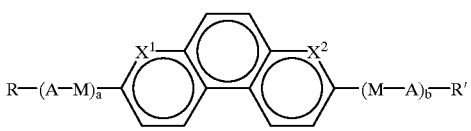

(II)

fluoropyridines of the formula (III),

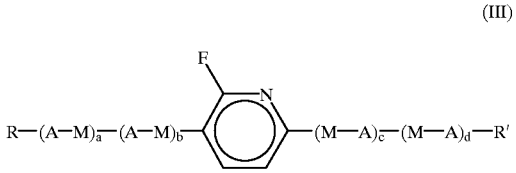

(III)

difluorophenylene derivatives of the formula (IV),

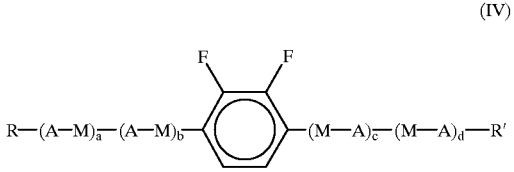

(IV)

meta-substituted aromatic compounds of the formula (V),

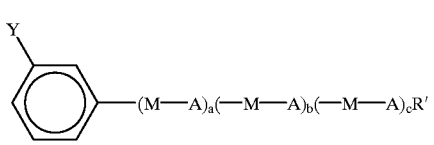

(V)

4-cyanocyclohexyls of the formula (VI),

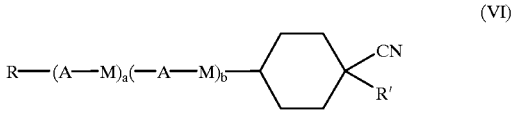

(VI)

1,3,4-thiadiazoles of the formula (VII)

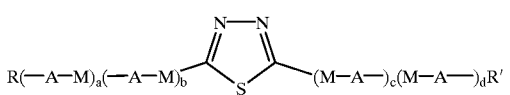

(VII)

where the symbols and indices have the following meanings:
$X^1$ and $X^2$ are identical or different and independently of one another are CH, CF or N,
Y is F, $CF_3$ oder R
R and R' are identical or different and independently of one another are as defined for $R^1$ and $R^2$ in formula (I),
A and M are identical or different and independently of one another are defined as in formula (I), and
a,b,c,d are identical or different and independently of one another are 0 or 1, with the proviso that the compounds may contain no more than four ring systems and must, with the exception of the formula (II), contain at least two ring systems.

The mixtures can in turn be employed in electrooptical or fully optical elements, for example display elements, switching elements, light modulators, elements for image processing and/or signal processing or, generally, in the area of nonlinear optics.

The novel ferroelectric liquid-crystal mixtures are particularly suitable for operation in the so-called inverse mode or $\tau V_{(min)}$ mode (see for example: J. C. Jones, M. J. Towler, J. R. Hughes, *Displays* 1993, 14, No. 2, 86–93; M. Koden, *Ferroelectrics* 1996, 179, 121–129).

In addition the mixtures are suitable for field treatment, i.e. for operation in the quasi-bookshelf geometry (QBG) (see, for example: H. Rieger et al., SID 91 Digest, Anaheim 1991, 396).

Liquid-crystalline mixtures comprising compounds of the formula (I) are particularly suitable for use in electrooptical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they comprise spacers, adhesive frames, polarizers and—for color displays—thin color-filter layers. Other possible components are antireflection, passivation, compensation and barrier layers and electric nonlinear elements, such as thin-film transistors (TFTs) and metal-insulator-metal (MIM) elements. The structure of liquid-crystal displays has already been described in detail in relevant monographs (see, for example: E. Kaneko, "*Liquid Crystal TV Displays: Principles and Applications of Liquid Crystal Displays*". KTK Scientific Publishers, 1987).

The invention therefore additionally provides a switching and/or display device, preferably a smectic or nematic, especially a ferroelectric device, comprising a liquid-crystal mixture which comprises one or more compounds of the formula (I).

In devices, which contain nematic liquid crystal mixtures, active matrix displays and in-plane-switching displays (IPS-LCD) are preferred.

In devices, which contain smectic liquid crystal mixtures, ECB displays (electrically controlled birefringence), electroclinic displays and chirally inclined smectic (ferroelectric or antiferroelectric) displays are preferred.

Such devices are e.g. applicable for computer displays or in chip-cards.

The novel switching and/or display device is preferably operated in normal mode or inverse mode.

Ferroelectric switching and/or display devices operated by multiplex addressing can inter alia be operated in two different ways, the normal mode or the inverse mode (or $\tau V_{(min)}$ mode). The difference between the two is in the addressing scheme and in the various requirements regarding the dielectric tensor of the FLC material, i.e. the FLC mixture. An overview is given, for example, by J. C. Jones et al. in *Displays* 1993, 14, No. 2, 86–93, referred to below as Jones, and M. Koden in *Ferroelectrics* 1996, 179, 121–129, and the literature set out therein.

The response characteristics of an FLC device can be generally represented in a diagram in which the driver voltage (V) is plotted horizontally and the width of the driving pulse ($\tau$, time) is plotted vertically (see for example Jones, FIGS. 4, 8, 10 and 11).

A response curve is determined experimentally and divides the V, $\tau$ area into a switching region and a nonswitching region. Normally, the pulse width becomes shorter when the voltage is increased. It is this behavior which characterizes the mode known as normal (see for example Jones, FIG. 4).

With appropriate materials, however, the V curve has a minimum (at the voltage $V_{(min)}$), as can be seen in Jones, for example, in FIGS. 8, 10 and 11. This minimum comes about as the result of the superimposition of dielectric and ferroelectric twisting. FLC devices are operated in the inverse mode if the sum of the row driver voltage and column driver voltage in the operating temperature range is higher than the minimum on the V, τ curve, i.e. $V_{(row)}+V_{(column)}>V_{(min)}$.

Express reference is made to the literature references cited in this application, especially regarding the synthesis of compounds of the formula (I); their citation makes them part of the description.

In the present application are cited various documents, e.g. to illustrate the technological surrounding of the invention. All these documents are specially related to this invention, they are part of the application by reference.

Also related to the invention is the content of German application no. 196 53 008.3, the priority thereof is claimed in this application, and the abstract of this application; all are part of the application by reference.

The invention is illustrated in more detail by means of the following examples, although this is not intended to represent a limitation.

The following abbreviations are used:

| | |
|---|---|
| abs. | absolute |
| DAST | diethylaminosulfur trifluoride |
| DCC | N,N'-dicyclohexylcarbodiimide |
| DDQ | 2,3-dichloro-5,6-dicyanobenzoquinone |
| DMAP | 4-dimethylaminopyridine |
| DMF | N,N-dimethylformamide |
| THF | tetrahydrofuran |

EXAMPLE 1
9-Fluoro-2,7-dioctyl-9,10-dihydrophenanthrene
From 2,7-dioctyl-9,10-dihydrophenanthren-9-ol by reaction with DAST in abs. dichloromethane.

EXAMPLE 2
9-Fluoro-2,7-dioctylphenanthrene
From 9-fluoro-2,7-dioctyl-9,10-dihydrophenanthrene by dehydrogenation with DDQ in toluene.

EXAMPLE 3
9-Fluoro-2,7-dihexyloxy-9,10-dihydrophenanthrene
From 2,7-dihexyloxy-9,10-dihydrophenanthren-9-ol by reaction with DAST in abs. dichloromethane.

EXAMPLE 4
9-Fluoro-2,7-dihexyloxyphenanthrene
From 9-fluoro-2,7-dihexyloxy-9,10-dihydrophenanthrene by dehydrogenation with DDQ in toluene.

EXAMPLE 5
9-Fluoro-2-hexyloxy-7-octylphenanthrene
From 9-fluoro-7-octylphenanthren-2-ol by reaction with 1-bromohexane and sodium hydride in abs. DMF.

EXAMPLE 6
9-Fluoro-7-octylphenanthren-2-yl hexanoate
From 9-fluoro-7-octylphenanthren-2-ol by reaction with hexanoyl chloride.

EXAMPLE 7
9-Fluoro-7-octylphenanthren-2-yl trans4-pentylcyclohexanecarboxylate
From 9-fluoro-7-octylphenanthren-2-ol by reaction with trans-4-pentylcyclohexane-carboxylic acid, DCC and DMAP.

EXAMPLE 8
9-Fluoro-2-(2-(S)-fluorooctyloxy)-7-octylphenanthrene
From 9-fluoro-7-octylphenanthren-2-ol by reaction with 2-(S)-fluorooctan-1-ol by Mitsunobu reaction.

EXAMPLE 9
9-Fluoro-7-(4-hexylphenyl)-2-octyloxyphenanthrene
From 7-bromo-9-fluoro-2-octyloxyphenanthrene by reaction with 4-hexylphenyl-boronic acid, sodium carbonate and tetrakis(triphenylphosphine)palladium(O) in toluene/ethanol/$H_2O$.

EXAMPLE 10
9-Fluoro-7-(2,3-difluoro4-octyloxyphenyl)-2-octyloxyphenanthrene
From 7-bromo-9-fluoro-2-octyloxyphenanthrene by reaction with 2,3-difluoro4-octyloxyphenylboronic acid, sodium carbonate and tetrakis(triphenylphosphine)-palladium (0) in toluene/ethanol/$H_2O$.

EXAMPLE 11
9-Fluoro-7-(6-hexyloxypyrid-3-yl)-2-octyloxyphenanthrene
From 7-bromo-9-fluoro-2-octyloxyphenanthrene by reaction with 6-hexyloxypyridine-3-boronic acid, sodium carbonate and tetrakis(triphenylphosphine)palladium(0) in toluene/ethanol/$H_2O$.

What is claimed is:
1. A fluorinated phenanthrene derivative of the formula (I)

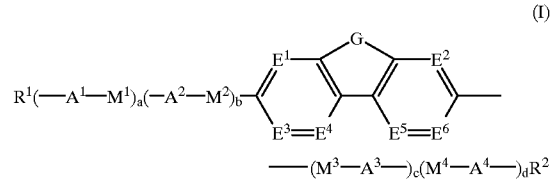

(I)

in which the symbols and indices have the following meanings:

G is —CHF—$CH_2$— or —CF=CH—;

$E^1$, $E^2$, $E^3$, $E^4$, $E^5$ and $E^6$ are identical or different and are —CH—, —CF— or —N—, with the proviso that $E^4$ and $E^5$ cannot simultaneously be —N—;

$R^1$ and $R^2$ are identical or different and are
a) hydrogen, —F, —Cl, —$CF_3$, —$OCF_3$ or —CN,
b) a straight-chain or branched alkyl radical (with or without an asymmetric carbon atom) having 1 to 20 carbon atoms, where
b1) one or more nonadjacent and nonterminal $CH_2$ groups can be replaced by —O—, —S—, —CO—O—, —O—CO—, —O—CO—O— or —Si($CH_3$)$_2$—, and/or
b2) one or more $CH_2$ groups can be replaced by —CH=CH—, —C≡C—, cyclopropane-1,2-diyl, 1,4-phenylene, 1,4-cyclohexylene or 1,3-cyclopentylene, and/or
b3) one or more H atoms can be replaced by F and/or Cl, and/or b4) the terminal CH$_3$ group can be replaced by one of the following chiral groups (optically active or racemic):

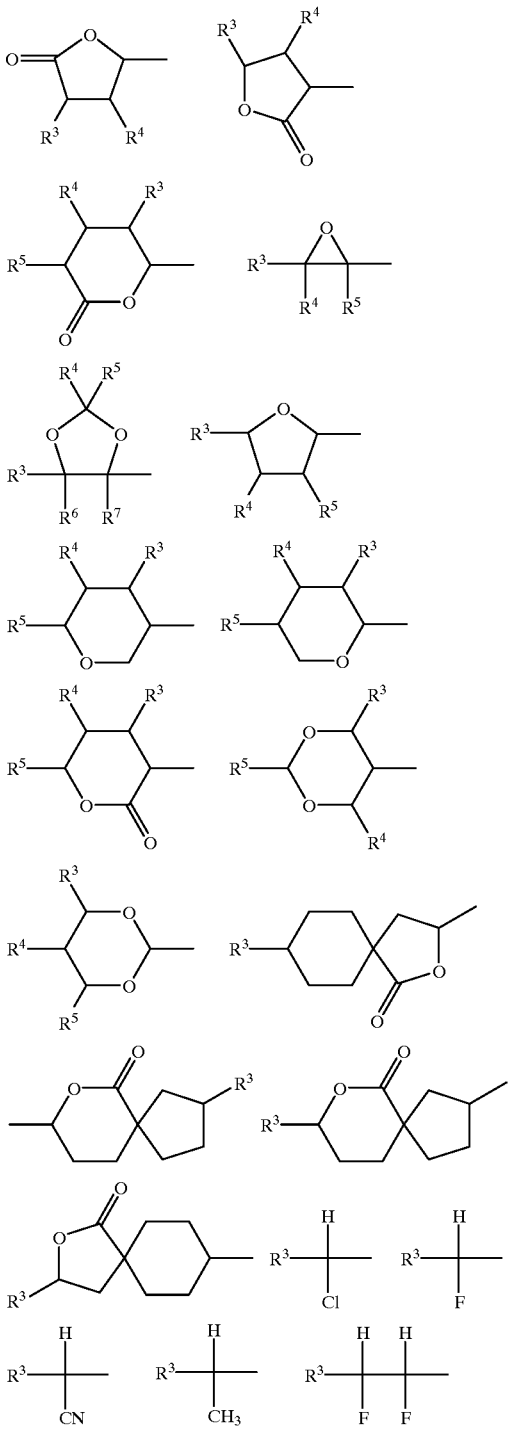

with the proviso that only one of the radicals R$^1$, R$^2$ can be hydrogen, —F, —Cl, —CF$_3$, —OCF$_3$ or —CN;

R$^3$, R$^4$, R$^5$, R$^6$ and R$^7$ are identical or different and are
a) hydrogen,
b) a straight-chain or branched alkyl radical (with or without an asymmetric carbon atom) having 1 to 16 carbon atoms, where b1) one or more nonadjacent and nonterminal CH$_2$ groups can be replaced by —O—, and/or
b2) one or two CH$_2$ groups can be replaced —CH=CH—, c) R$^4$ and R$^5$ together are alternatively —(CH$_2$)$_4$— or —(CH$_2$)$_5$—, if they are attached to an oxirane, dioxolane, tetrahydrofuran, tetrahydropyran, butyrolactone or valerolactone system;

M$^1$, M$^2$, M$^3$ and M$^4$ are identical or different and are —CO—O—, —O—CO—, —CO—S—, —S—CO—, —CS—O—, —O—CS—, —CH$_2$—O—, —O—CH$_2$—, —CH$_2$—S—, —S—CH$_2$—, —CH=CH—, —C≡C—, —CH$_2$—CH$_2$—CO—O—, —O—CO—CH$_2$—CH$_2$— or a single bond;

A$^1$, A$^2$, A$^3$ and A$^4$ are identical or different and are 1,4-phenylene in which one or more H atoms can be replaced by F, Cl and/or CN, pyrazine-2,5-diyl, in which one or two H atoms can be replaced by F, Cl and/or CN, pyridazine-3,6-diyl in which one or two H atoms can be replaced by F, Cl and/or CN, pyridine-2,5-diyl in which one or more H atoms can be replaced by F, Cl and/or CN, pyrimidine-2,5-diyl in which one or two H atoms can be replaced by F, Cl and/or CN, 1,4-cyclohexylene in which one or two H atoms can be replaced by CN, F and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom can be replaced by F, Cl and/or CN, 1,3-thiazole-2,5-diyl in which one H atom can be replaced by F, Cl and/or CN, thiophene-2,4-diyl, in which one H atom can be replaced by F, Cl and/or CN, thiophene-2,5-diyl in which one or two H atoms can be replaced by F, Cl and/or CN, piperazine-1,4-diyl piperazine-2,5-diyl or 1-(C$_1$–C$_4$)alkyl-1-silacyclohexylene-1,4-diyl;

a, b, c and d are zero or one,
with the proviso that the compound of the formula (I) may contain no more than four ring systems having five or more members.

2. A fluorinated phenanthrene derivative as claimed in claim 1, wherein the symbols and indices in the formula (I) have the following meanings:

E$^1$ and E$^2$ are identical or different and are —CH—, —CF— or —N— and E$^3$, E$^4$, E$^5$ and E$^6$ are identical or different and are —CH— or —CF—, R$^1$ and R$^2$ are identical or different and are
a) hydrogen, —CN or F,
b) a straight-chain or branched alkyl radical (with or without an asymmetric carbon atom) having 1 to 18 carbon atoms, where
b1) one or more nonadjacent and nonterminal CH$_2$ groups can be replaced by —O—, —CO—O—, —O—CO—, —O—CO—O or —Si(CH$_3$)$_2$—, and/or
b2) one CH$_2$ group can be replaced by cyclopropane-1,2-diyl, 1,4-phenylene or trans-1,4-cyclohexylene, and/or
b3) one or more H atoms can be replaced by F, and/or
b4) the terminal CH$_3$ group can be replaced by one of the following chiral groups (optically active or racemic):

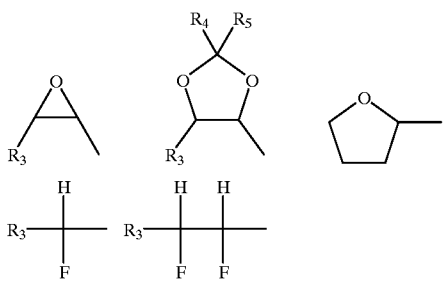

with the proviso that only one of the radicals $R^1$ and $R^2$ can be —H, —F or —CN;

$R^3$, $R^4$, $R^5$, $R^6$ and $R^7$ are identical or different and are
  a) hydrogen,
  b) a straight-chain or branched alkyl radical (with or without an asymmetric carbon atom) having 1 to 14 carbon atoms, where
    b1) one or two nonadjacent and nonterminal $CH_2$ groups can be replaced by —O—, and/or
    b2) one $CH_2$ group can be replaced by —CH═CH—,
  c) $R^4$ and $R^5$ together are alternatively —$(CH_2)_4$— or —$(CH_2)_5$—, if they are attached to an oxirane, dioxolane, tetrahydrofuran, tetrahydropyran, butyrolactone or valerolactone system;

$M^1$, $M^2$, $M^3$ and $M^4$ are identical or different and are —CO—O—, —O—CO—, —$CH_2$—O—, —O—$CH_2$—, —CH═CH—, —C≡C—, —$CH_2$—$CH_2$—CO—O, —O—CO—$CH_2$—$CH_2$— or a single bond;

$A^1$, $A^2$, $A^3$ and $A^4$ are identical or different and are 1,4-phenylene in which one or two H atoms can be replaced by F and/or CN, pyridine-2,5-diyl, in which one or two H atoms can be replaced by F and/or CN, pyrimidine-2,5-diyl in which one or two H atoms can be replaced by F and/or CN, trans-1,4-cyclohexylene in which one or two H atoms can be replaced by CN and/or F, 1,3,4-thiadiazole-2,5-diyl, 1,3-dioxane-2,5-diyl, 1,3-thiazole-2,4-diyl, in which one H atom can be replaced by F, 1,3-thiazole-2,5-diyl in which one H atom can be replaced by F, or thiophene-2,5-diyl in which one or two H atoms can be replaced by F;

a, b, c and d are zero or one,
  with the proviso that the compound of the formula (I) may contain no more than four ring systems having five or more members.

3. A fluorinated phenanthrene derivative as claimed in claim 1, wherein the symbols and indices in the formula (I) have the following meanings:

$E^1$ and $E^2$ are identical or different and are —CH— or —CF— or —N— and $E^3$, $E^4$, $E^5$ and $E^6$ are —CH—;

$R^1$ and $R^2$ are identical or different and are
  a) hydrogen,
  b) a straight-chain or branched alkyl radical (with or without an asymmetric carbon atom) having 1 to 16 carbon atoms, where
    b1) one or two nonadjacent and nonterminal $CH_2$ groups can be replaced by —O—, —CO—O—, —O—CO—, —O—CO—O— or —Si$(CH_3)_2$—, and/or
    b2) one $CH_2$ group can be replaced by 1,4-phenylene or trans-1,4-cyclohexylene, and/or
    b3) one or more H atoms can be replaced by F, and/or
    b4) the terminal $CH_3$ group can be replaced by one of the following chiral groups (optically active or racemic):

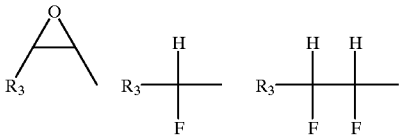

with the proviso that only one of the radicals $R^1$ and $R^2$ can be H;

$R^3$, $R^4$, $R^5$, $R^6$ and $R^7$ are identical or different and are
  a) hydrogen,
  b) a straight-chain or branched alkyl radical (with or without an asymmetric carbon atom) having 1 to 14 carbon atoms, where
    b1) one nonterminal $CH_2$ group can be replaced by —O—, and/or
    b2) one $CH_2$ group can be replaced by —CH═CH—,
  c) $R^4$ and $R^5$ together are alternatively —$(CH_2)_4$— or —$(CH_2)_5$—, if they are attached to an oxirane, dioxolane, tetrahydrofuran, tetrahydropyran, butyrolactone or valerolactone system;

$M^1$, $M^2$, $M^3$ and $M^4$ are identical or different and are —CO—O—, —O—CO—, —$CH_2$—O—, —O—$CH_2$— or a single bond;

$A^1$, $A^2$, $A^3$, $A^4$ are identical or different and are
  1,4-phenylene in which one or two H atoms can be replaced by F, pyridine-2,5-diyl in which one H atom can be replaced by F, pyrimidine-2,5-diyl, trans-1,4-cyclohexylene in which one or two H atoms can be replaced by CN and/or F, 1,3,4-thiadiazole-2,5-diyl, 1,3-thiazole-2,4-diyl or thiophene-2,5-diyl;

a, b, c and d are zero or one,
  with the proviso that the compound of the formula (I) contains no more than four ring systems having five or more members.

4. A fluorinated phenanthrene derivative as claimed in claim 1, which is selected from the group consisting of (Ia)–(If):

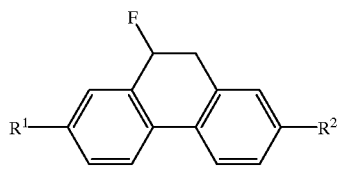

(Ia)

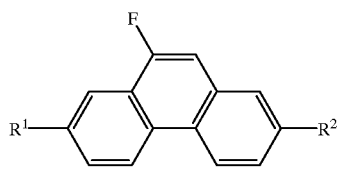

(Ib)

(Ic)
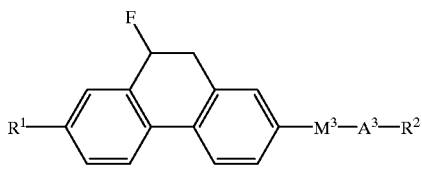

(Id)
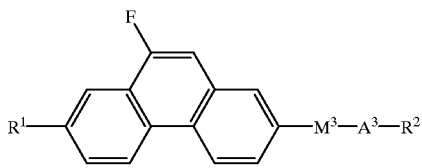

(Ie)
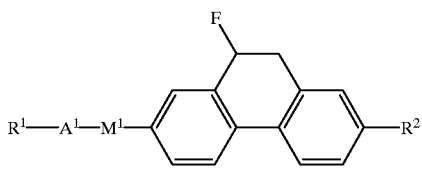

(If)
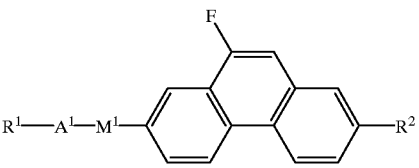

in which $R^1$, $R^2$, $M^1$, $M^3$, $A^1$ and $A^3$ have the meanings stated in claim 1.

5. A liquid-crystal mixture comprising one or more fluorinated phenanthrene derivatives as claimed in claim 1.

6. A liquid crystal mixture as claimed in claim 5, which is ferroelectric.

7. A liquid-crystal mixture as claimed in claim 5, which contains from 0.01 to 80% by weight of one or more fluorinated phenanthrene derivatives of the formula (I).

8. A ferroelectric switching and/or display device comprising a ferroelectric liquid-crystal mixture as claimed in claim 6.

9. A ferroelectric switching and/or display device as claimed in claim 8, which is operated in the $\tau V_{(min)}$ mode.

* * * * *